(12) United States Patent
Lankton

(10) Patent No.: US 6,512,151 B2
(45) Date of Patent: *Jan. 28, 2003

(54) PROCESS FOR THE PURIFICATION AND PRODUCTION OF A DIOLEFIN HYDROCARBON STREAM

(75) Inventor: Steven P. Lankton, Wheeling, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/823,747

(22) Filed: Apr. 18, 2001

(65) Prior Publication Data

US 2002/0177746 A1 Nov. 28, 2002

(51) Int. Cl.[7] .............................. C07C 5/03; C07C 7/163
(52) U.S. Cl. ......................... 585/259; 585/262; 585/258
(58) Field of Search ................................. 585/259, 262, 585/258

(56) References Cited

U.S. PATENT DOCUMENTS

| 3,634,536 A | 1/1972 | Frevel et al. | ......... 260/681.5 R |
|---|---|---|---|
| 4,440,956 A | 4/1984 | Couvillion | ................... 585/260 |
| 6,040,489 A | * 3/2000 | Imai | ............................ 203/29 |

OTHER PUBLICATIONS

U.S. Application No. 09358,795 (Cottrell) Filed Jul. 22, 1999.
U.S. Application No. 09/359,629 (Cottrell) Filed Jul. 22, 1999.

* cited by examiner

*Primary Examiner*—Thuan D. Dang
(74) *Attorney, Agent, or Firm*—John G. Tolomei; James C. Paschall; John G. Cutts, Jr.

(57) ABSTRACT

A selective acetylene hydrogenation process which is able to produce a high quality diolefin having extremely low levels of acetylene over an extended period of time compared with the prior art. The process of the present invention provides a selective hydrogenation reaction zone wherein the catalyst activity is maintained at a high level while the process unit remains on stream by contacting the selective hydrogenation catalyst with a polymer solvent, diolefin feed and hydrogen in one embodiment and by contacting the selective hydrogenation catalyst off-line with only polymer solvent and hydrogen in a second embodiment. In addition, the quantity of make-up regeneration solvent is significantly reduced.

11 Claims, 1 Drawing Sheet

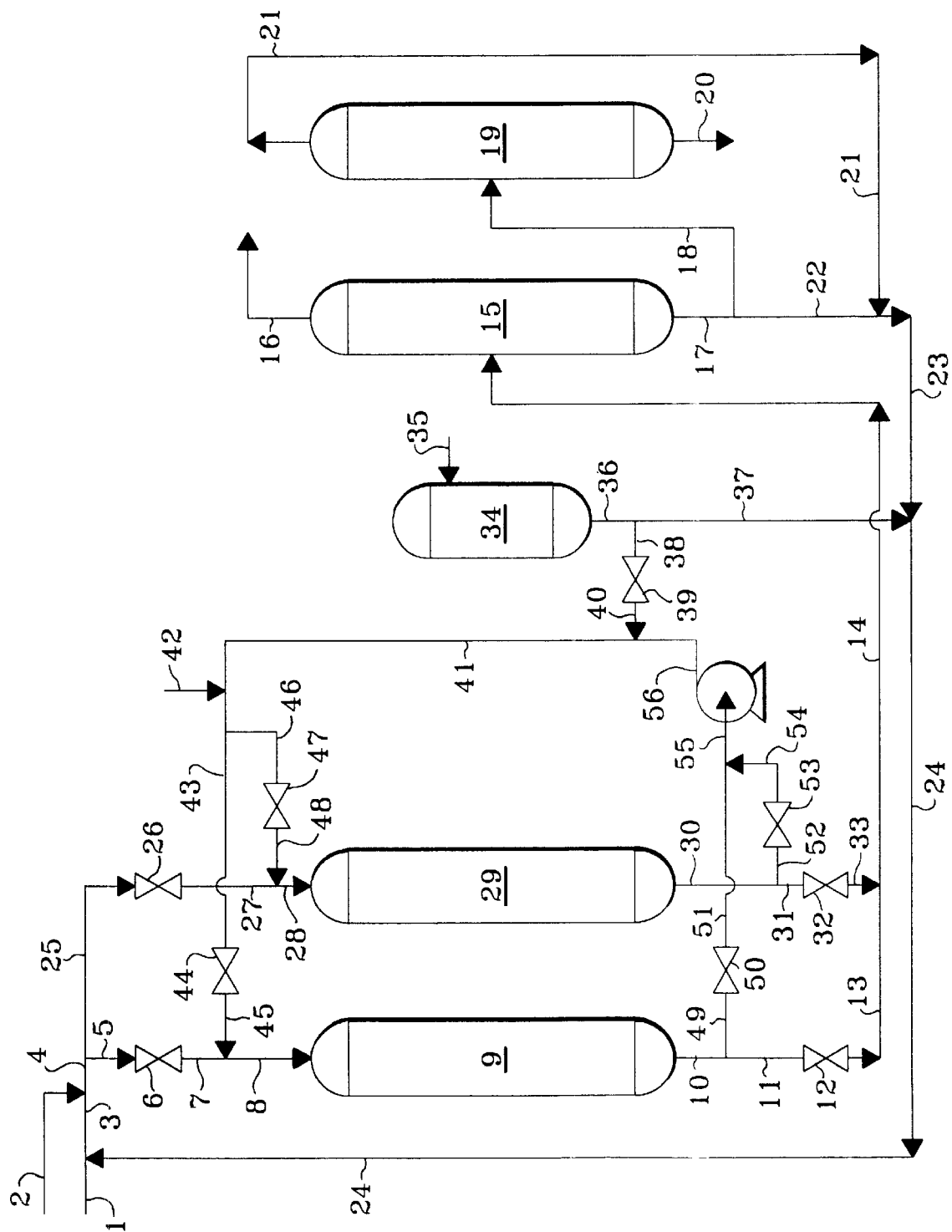

PROCESS FOR THE PURIFICATION AND PRODUCTION OF A DIOLEFIN HYDROCARBON STREAM

BACKGROUND OF THE INVENTION

The field of art to which this invention pertains is the purification of a diolefin hydrocarbon stream containing trace quantities of acetylene compounds. The production of diolefins is well known and widely practiced to produce a wide variety of products and precursor products utilizing a variety of diolefin production processes including naphtha cracking processes and by-products from fluid catalytic cracking processes. Most of these diolefin production processes produce undesirable trace quantities of acetylene. One technique which is used to purify diolefin streams selectively hydrogenates the acetylene while minimizing the destruction or hydrogenation of the diolefin compounds.

The selective hydrogenation of the acetylene compounds is generally conducted in the presence of a selective hydrogenation catalyst and hydrogen and conducted at an elevated pressure and temperature. Such selective hydrogenation catalysts are well known in the art and include, for example, a catalyst containing copper metal associated with one or more activator metals impregnated on an alumina support. During the acetylene hydrogenation polymers are formed and deposited on the catalyst thereby reducing the activity of the catalyst. One known method of regenerating spent or partially spent catalyst is to perform a controlled carbon burn and subsequent metal reduction to remove catalyst contaminants which are formed as an undesirable by-product of the acetylene hydrogenation. The carbon burn regeneration techniques necessarily require that the reaction zone containing the spent catalyst be taken off-line and that ancillary regeneration equipment be provided.

INFORMATION DISCLOSURE

U.S. Pat. No. 3,634,536 B1 (Frevel et al) discloses a process for selectively hydrogenating acetylenic impurities in an isopropene- or butadiene-containing stream whereby carbon monoxide is utilized during hydrogenation over a copper-based catalyst.

U.S. Pat. No. 4,440,956 B1 (Couvillion) discloses a catalyst for the removal of acetylenes from liquid hydrocarbon streams with a minimum loss of diolefinic unsaturation present in the liquid composition.

U.S. application Ser. No. 09/358,795 filed on Jul. 22, 1999 discloses a process for an on-line regeneration of a selective hydrogenation catalyst with a solvent.

U.S. application Ser. No. 09/359,629 filed on Jul. 22, 1999 discloses a process for an off-line regeneration of a selective hydrogenation catalyst with a solvent.

Although a wide variety of process flow schemes, operating conditions and catalysts have been used in commercial activities, there is always a demand for new selective hydrotreating processes which provide lower costs, higher selectivity and longer on-stream operation.

The present invention maintains the high activity of the selective hydrogenation catalyst during an extended run length. Higher average product quality when integrated over time on-stream improves the process economics and demonstrates the unexpected advantages. In addition, the quantity of make-up regeneration solvent is significantly reduced.

BRIEF SUMMARY OF THE INVENTION

The present invention is a selective acetylene hydrogenation process which is able to produce a high quality diolefin having extremely low levels of acetylene over an extended period of time compared with the prior art. The process of the present invention provides a selective hydrogenation reaction zone wherein the catalyst activity is maintained at a high level while the process unit remains on stream by contacting the selective hydrogenation catalyst with a polymer solvent, diolefin feed and hydrogen in one embodiment and by contacting the selective hydrogenation catalyst off-line with only polymer solvent and hydrogen in a second embodiment.

In accordance with one embodiment, the present invention relates to a process for the purification of a diolefin hydrocarbon feed stream containing trace quantities of acetylene compounds which process comprises: (a) contacting the diolefin hydrocarbon feed stream containing trace quantities of acetylene compounds and hydrogen with a selective hydrogenation catalyst in a selective hydrogenation zone to selectively hydrogenate at least a portion of the acetylene compounds; (b) contacting the resulting selective hydrogenation catalyst containing polymer compounds produced in step (a) with a polymer solvent and hydrogen to produce a stream comprising polymer solvent and dissolved polymer compounds;, (c) separating the stream comprising polymer solvent and dissolved polymer compounds to produce a stream comprising polymer solvent and having a reduced concentration of polymer compounds, and a stream rich in polymer compounds; (d) recycling at least a portion of the stream comprising polymer solvent and having a reduced concentration of polymer compounds to step (b) to supply at least a portion of the polymer solvent; (e) recovering the stream rich in polymer compounds produced in step (c); and (f) recovering a diolefin hydrocarbon stream having a reduced concentration of acetylene compounds produced in step (a).

In accordance with another embodiment, the present invention relates to a process for the purification of a diolefin hydrocarbon feed stream containing trace quantities of acetylene compounds which process comprises: (a) contacting the diolefin hydrocarbon feed stream containing trace quantities of acetylene compounds with a polymer solvent and introducing: the resulting admixture together with elemental hydrogen into a selective hydrogenation zone containing a selective hydrogenation catalyst to selectively hydrogenate at least a portion of the acetylene compounds; (b) passing the resulting effluent from the selective hydrogenation zone in step (a) to a first fractionation zone to produce a diolefin hydrocarbon stream having a reduced concentration of acetylene compounds and a stream containing polymer solvent and polymer compounds; (c) recycling at least a portion of the stream containing polymer solvent and polymer compounds to provide at least a portion of the polymer solvent in step (a); (d) passing at least another portion of the stream containing polymer solvent and polymer-compounds to a second fractionation zone to produce a stream containing polymer solvent and having a reduced concentration of polymer compounds, and a stream containing polymer solvent and having an increased concentration of polymer compounds; (e) recovering the stream containing polymer solvent and having an increased concentration of polymer compounds; and (f) recovering the diolefin hydrocarbon stream having a reduced concentration of acetylene compounds produced in step (b).

In yet another embodiment, the present invention relates to a process for the purification of a butadiene hydrocarbon feed stream containing trace quantities of acetylene compounds which process comprises: (a) contacting the butadiene hydrocarbon feed stream containing trace quantities of acetylene compounds and hydrogen with a selective hydrogenation catalyst in a selective hydrogenation zone to selectively hydrogenate at least a portion of the acetylene compounds; (b) contacting the resulting selective hydrogenation catalyst containing polymer compounds produced in step (a) with a polymer solvent comprising an alkane having from 4 to about 8 carbon atoms and hydrogen to produce a stream comprising polymer solvent and dissolved polymer compounds; (c) separating the stream comprising polymer solvent and dissolved polymer compounds to produce a stream comprising polymer solvent and having a reduced concentration of polymer compounds, and a stream rich in polymer compounds; (d) recycling at least a portion of the stream comprising polymer solvent and having a reduced concentration of polymer compounds to step (b) to supply at least a portion of the polymer solvent; (e) recovering the stream rich in polymer compounds produced in step (c); and (f) recovering a butadiene hydrocarbon stream having a reduced concentration of acetylene compounds produced in step (a).

BRIEF DESCRIPTION OF THE DRAWING

The drawing is a simplified process flow diagram of a preferred embodiment of the present invention. The drawing is intended to be, schematically illustrative of the present invention and not be a limitation thereof.

DETAILED DESCRIPTION OF THE INVENTION

It has been previously discovered that a selective hydrogenation is Zone for the hydrogenation of trace quantities of acetylene contained in a stream of diolefins may achieve continued start-of-run activity, yield and product quality by contacting the selective catalyst with a polymer solvent and hydrogen. These advantages enable superior performance and economic results. However, the circulating polymer solvent becomes contaminated with polymer compounds and a bleed or slipstream must be removed from the polymer solvent inventory to prevent undesirable high concentrations of polymer compounds in the polymer solvent. In order to remove an amount of polymer compounds in the slipstream equal to the incoming polymer compounds, the slipstream also contains a significantly large amount of solvent which must be replaced in order to maintain the polymer solvent inventory. This addition of polymer solvent is an onerous burden and imposes a heavy economic penalty. In accordance with the present invention, the amount of make-up polymer solvent is greatly reduced and permits the recovery and recycle of the polymer solvent.

The process of the present invention is particularly useful for the production of high quality diolefin streams in a process having an extended on-stream capability. The diolefin feed stream may be any convenient hydrocarbon stream containing diolefin compounds and having undesirable trace quantities of acetylene compounds. It is contemplated that the diolefin feedstream contains diolefins containing from 3 to about 5 carbon atoms. A preferred diolefin feedstream contains butadiene.

In accordance with one embodiment of the present invention, the selected diolefin feedstock is introduced along with a polymer solvent and hydrogen into a selective hydrogenation reaction zone operating at selective hydrogenation conditions and containing a selective hydrogenation catalyst to produce an improved diolefin stream having a reduced concentration of acetylene compounds. In another embodiment, a deactivated selective hydrogenation reaction zone is removed from hydrogenation service, contacted with a polymer solvent and hydrogen to at least partially restore the catalyst activity and then reintroduced into hydrogenation service. This catalyst regeneration preferably includes conditions with a pressure from about 150 psig to about 600 psig, a temperature from about 90° F. to about 500° F. and a solvent liquid hourly space velocity from about 0.5 to about 10 $hr^{-1}$. The second fractionation zone is preferably operated under vacuum conditions including a pressure from about 2 to about 14 psia to preferably remove less than about 1.0 and more preferably less than about 0.1; weight percent of the polymer solvent based on the diolefin hydrocarbon feed stream from the process.

The polymer solvent may be selected from any compound or mixtures of compounds and which polymer solvent is capable of acting as a solvent for polymers which are produced during the selective hydrogenation reaction. Suitable solvents may be selected from alkane compounds having from about 4 to about 8 or more carbon atoms. In the case where the fresh feedstock is a stream of butadiene, a particularly preferred polymer solvent is hexane. The polymer solvent may be present in the selective hydrogenation zone in an amount of about 5 to about 200 weight percent based on the weight of diolefin. It is preferred that the polymer solvent has a boiling point greater than the diolefin feedstream. The selective hydrogenation conditions will depend upon the selected diolefinic feed and may be selected from a pressure from about 200 psig to about 600 psig and a temperature from about 90° F. to about 180° F.

The resulting effluent from the selective hydrogenation reaction zone is passed to a fractionation zone to produce a diolefin hydrocarbon stream having a reduced concentration of acetylene compounds and a stream containing the polymer solvent and polymer compounds. At least a portion of the polymer solvent recovered from the fractionation zone is recycled to the inlet of the selective hydrogenation zone. A drag stream of polymer solvent containing dissolved polymer compounds and in a sufficient amount to prevent undesirable buildup of polymer compounds is introduced into a second fractionation zone to produce a polymer solvent stream having a reduced concentration of polymer compounds and a concentrated stream comprising polymer compounds which is removed from the process to prevent an accumulation of polymer compounds in the polymer solvent. At least a portion of the polymer solvent stream having a reduced concentration of polymer compounds is recycled. Fresh make-up polymer solvent is added to maintain a suitable inventory of solvent.

DETAILED DESCRIPTION OF THE DRAWING

In the drawing, the process of the present invention is illustrated by means of a simplified schematic flow diagram in which such details :as instrumentation, heat-exchange, and heat-recovery circuits, separation facilities and similar hardware have been deleted as being non-essential to an understanding of the techniques involved.

With reference now to the drawing, a feed stream comprising butadiene and trace quantities of acetylene is introduced into the process via line 1 and is admixed with a polymer solvent comprising hexane carried via line 24 and the resulting admixture is carried via line 3 and is then admixed with a hydrogen-rich gaseous stream introduced via line 2. This resulting admixture is carried via lines 4 and 5, valve 6 and lines 7 and 8 and introduced into selective hydrogenation zone 9. A stream containing a reduced concentration of acetylene compounds is removed from selective hydrogenation zone 9 via lines 10 and 11, valve 12 and lines 13 and 14 and is introduced into fractionation zone 15. A product stream comprising butadiene is removed from fractionation zone 15 via line 16 and recovered. A polymer solvent comprising hexane and dissolved polymer compounds is removed from fractionation zone 15 via line 17 and a portion is carried via lines 22, 23 and 24 and recycled to the inlet of selective hydrogenation zone 9 as hereinabove described. Another portion of the polymer solvent containing hexane and polymer compounds which is removed from fractionation zone 15 via line 17 is transported via line 18 and introduced into fractionation zone 19. A polymer solvent stream having a reduced concentration of polymer compounds is removed from fractionation zone 19 via line 21 and is recycled via lines 23 and 24 to the inlet of the selective hydrogenation zone 9 as hereinabove described. A stream comprising polymer compounds is removed from fractionation zone 19 via line 20 and recovered. Make-up polymer solvent containing hexane is introduced via line 35 into polymer solvent storage vessel 34. A stream of polymer solvent is removed from polymer solvent storage vessel 34 via line 36 and a portion is carried via line 38, valve 39, line 40, 41 and is admixed with a hydrogen-rich gaseous stream introduced via line 42. The resulting admixture is carried via line 46, valve 47 and lines 48 and 28 and is introduced into selective hydrogenation zone 29 which is off-line and being regenerated as presently described. A polymer solvent stream containing polymer compounds is removed from selective hydrogenation zone 29 via lines 30 and 52, valve 53, line 54 and 55, pump 56 and line 41 and is circulated to the inlet of selective hydrogenation zone 29 as hereinabove described. When the catalyst in selective hydrogenation zone 9 becomes spent and it is desired to introduce the butadiene feed, hydrogen and polymer solvent into selective hydrogenation zone 29, valves 6 and 12 are closed to isolate selective hydrogenation zone 9 and the feed stream is then carried via lines 4 and 25, valve 26 and lines 27 and 28 and introduced into selective hydrogenation zone 29. A stream containing butadiene and having a reduced concentration of acetylene compounds is removed from selective hydrogenation zone 29 via lines 30 and 31, valve 32 and lines 33 and 14 and introduced into fractionation zone 15. A stream of polymer solvent is carried via lines 36 and 38, valve 39, line 40 and 41 and is admixed with a hydrogen-rich gaseous stream introduced via line 42 and the resulting admixture is carried via line 43, valve 44 and lines 45 and 8 and introduced into selective hydrogenation zone 9. A stream containing polymer solvent and dissolved polymer compounds is removed from selective hydrogenation zone 9 via lines 10 and 49, valve 50, lines 51 and 55, pump 56, lines 41 and 43 and circulated as described hereinabove. A stream of polymer solvent is carried via lines 37 and 24, and introduced into selective hydrogenation zone 9 as described before.

EXAMPLES

The following examples are presented to demonstrate the advantages of the present invention. Example 1 is a prior art process for the purification of a diolefin hydrocarbon feed stream which requires the use and disposal of large quantities of polymer solvent. Example 2 demonstrates an improved process for the purification of the same diolefin hydrocarbon feed stream which is one embodiment of the present invention but is not presented to unduly limit the present invention. The following results were not obtained by the actual performance of the present invention but are considered prospective and reasonably illustrative of the expected performance of the 5 invention based upon sound engineering calculations.

EXAMPLE 1

In a prior art process for the purification of the butadiene hydrocarbon stream, a fresh feedstock having the characteristics and flow rate presented in Table 1 is admixed with 20240 Kg/hr of hexane solvent and 10.5 Kg/hr of hydrogen and introduced into a selective hydrogenation zone containing a selective hydrogenation catalyst containing copper. The resulting effluent from the selective hydrogenation zone which contains an additional 10.1 Kg/hr of green oil produced in the selective hydrogenation zone is introduced into a solvent recovery column to produce a butadiene product stream having the composition and flow rate presented in Table 2 and to recover a hexane solvent stream containing green oil and at least a portion is recycled to the inlet of the selective hydrogenation zone. A small light gaseous stream containing hydrogen, 1-butene and 1,3 butadiene in an amount of 57 Kg/hr is produced and recovered. A slipstream of the circulating hexane solvent containing green oil in an amount of 1610 Kg/hr including 1575 Kg/hr of hexane, 14.1 Kg/hr of green oil and 19.3 Kg/hr of butadiene is removed from the process in order to purge the green oil and prevent its buildup in the circulating hexane solvent. In order to maintain the circulating hexane solvent, a fresh make-up stream of 1575 Kg/hr of hexane is required. This hexane solvent make-up rate is about 7.7 weight percent of the butadiene feed rate.

Example 2

The process described in Example 1 was repeated with an additional step whereby the same slipstream of the circulating hexane solvent containing green oil is introduced into a drag stream fractionation zone to produce a drag.-stream in an amount of 32 Kg/hr including 16.1 Kg/hr of hexane and 14.1 Kg/hr of green oil. The balance of the hexane or 1558.9 Kg/hr is recovered to serve as circulating hexane solvent. Therefore, only 16.1 Kg/hr of fresh make-up hexane is required. This solvent make-up rate is only about 0.001 weight percent of the butadiene feed rate.

TABLE 1

FEEDSTOCK COMPOSITION AND FLOW RATE

| Component | Flow Rate, Kg/hr |
| --- | --- |
| Propadiene | 0.1 |
| Propene | — |
| Methyl Acetylene | 1.0 |
| 1-Butene | 81.0 |
| 1,3 Butadiene | 20150 |
| Ethyl Acetylene | 1.6 |
| Vinyl Acetylene | 0.4 |
| Green Oil | 4.0 |
| Residue | 2.0 |
| Total, Kg/hr | 20240 |

TABLE 2

BUTADIENE PRODUCT COMPOSITION AND FLOW RATE

| Component | Flow Rate, Kg/hr |
| --- | --- |
| Hydrogen | 1.3 |
| Propadiene | 0.1 |

TABLE 2-continued

BUTADIENE PRODUCT COMPOSITION AND FLOW RATE

| Component | Flow Rate, Kg/hr |
|---|---|
| Propene | 1.0 |
| Methyl Acetylene | — |
| 1-Butene | 135.2 |
| 1,3 Butadiene | 20021 |
| Hexane | 1.7 |
| Total, Kg/hr | 20160 |

The foregoing description, drawing and examples clearly illustrate the advantages encompassed by the process of the present invention and the benefits to be afforded with the use thereof.

What is claimed:

1. A process for the purification of a diolefin hydrocarbon feed stream containing trace quantities of acetylene compounds which process comprises:
   (a) contacting the diolefin hydrocarbon feed stream containing trace quantities of acetylene compounds and hydrogen with a selective hydrogenation catalyst in a selective hydrogenation zone to selectively hydrogenate at least a portion of the acetylene compounds;
   (b) contacting the resulting selective hydrogenation catalyst containing polymer compounds produced in step (a) with a polymer solvent comprising an alkane having from 4 to about 8 carbon atoms and hydrogen to produce a stream comprising polymer solvent and dissolved polymer compounds;
   (c) separating the stream comprising polymer solvent and dissolved polymer compounds to produce a stream comprising polymer solvent and having a reduced concentration of polymer compounds, and a stream rich in polymer compounds;
   (d) recycling at least a portion of the stream comprising polymer solvent and having a reduced concentration of polymer compounds to step (b) to supply at least a portion of the polymer solvent;
   (e) recovering the stream rich in polymer compounds produced in step (c); and
   (F) recovering a diolefin hydrocarbon stream having a reduced concentration of acetylene compounds produced in step (a).

2. The process of claim 1 wherein the diolefin feed stream comprises butadiene.

3. The process of claim 1 wherein the selective hydrogenation zone contains a catalyst comprising copper.

4. The process of claim 1 wherein the selective hydrogenation zone is operated at conditions including a pressure from about 200 to about 600 psig and a temperature from about 90° F. to about 180° F.

5. The process of claim 1 wherein the stream rich in polymer compounds produced in step (c) contains polymer solvent in an amount less than about 0.1 weight percent of the diolefin hydrocarbon feed stream.

6. A process for the purification of a diolefin hydrocarbon feed stream containing trace quantities of acetylene compounds which process comprises:
   (a) contacting the diolefin hydrocarbon feed stream containing trace quantities of acetylene compounds with a polymer solvent comprising an alkane having from 4 to about 8 carbon atoms and introducing the resulting admixture together with elemental hydrogen into a selective hydrogenation zone containing a selective hydrogenation catalyst to selectively hydrogen at least a portion of the acetylene compounds;
   (b) passing the resulting effluent from the selective hydrogenation zone in step (a) to a first fractionation zone to produce a diolefin hydrocarbon stream having a reduced concentration of acetylene compounds and a stream containing polymer solvent and polymer compounds;
   (c) recycling at least a portion of the stream containing polymer solvent and polymer compounds to provide at least a portion of the polymer solvent in step (a);
   (d) passing at least another portion of the stream containing polymer solvent and polymer compounds to a second fractionation zone to produce a stream containing polymer solvent and having a reduced concentration of polymer compounds, and a stream containing polymer solvent and having an increased concentration of polymer compounds;
   (e) recovering the stream containing polymer solvent and having an increased concentration of polymer compounds; and
   (f) recovering the diolefin hydrocarbon stream having a reduced concentration of acetylene compounds produced in step (b)

7. The process of claim 6 wherein the diolefin feed stream comprises butadiene.

8. The process of claim 6 wherein the selective hydrogenation zone contains a catalyst comprising copper.

9. The process of claim 6 wherein the selective hydrogenation zone is operated at conditions including a pressure from about 200 to about 600 psig and a temperature from 90° F. to about 180° F.

10. The process of claim 6 wherein the stream containing polymer solvent and having an increased concentration of polymer compounds produced in step (d) contains polymer solvent in an amount less than about 0.1 weight percent of the diolefin hydrocarbon feed stream.

11. A process for the purification of a butadiene hydrocarbon feed stream containing trace quantities of acetylene compounds which process comprises:
   (a) contacting the butadiene hydrocarbon feed stream containing trace quantities of acetylene compounds and hydrogen with a selective hydrogenation catalyst in a selective hydrogenation zone to selectively hydrogenate at least a portion of the acetylene compounds;
   (b) contacting the resulting selective hydrogenation catalyst containing polymer compounds produced in step (a) with a polymer solvent comprising an alkane having from 4 to about 8 carbon atoms and hydrogen to produce a stream comprising polymer solvent and dissolved polymer compounds;
   (c) separating the stream comprising polymer solvent and dissolved polymer compounds to produce a stream comprising polymer solvent and having a reduced concentration of polymer compounds, and a stream rich in polymer compounds;
   (d) recycling at least a portion of the stream comprising polymer solvent and having a reduced concentration of polymer compounds to step (b) to supply at least a portion of the polymer solvent;
   (e) recovering the stream rich in polymer compounds produced in step (c); and recovering a butadiene hydrocarbon stream having a reduced concentration of acetylene compounds produced in step (a).

* * * * *